US007498297B2

(12) United States Patent
Szeto et al.

(10) Patent No.: US 7,498,297 B2
(45) Date of Patent: *Mar. 3, 2009

(54) MEDICINAL USES OF MU-OPIOID RECEPTOR AGONISTS

(75) Inventors: Hazel Szeto, New York, NY (US); Peter W. Schiller, Montreal (CA)

(73) Assignees: Cornell Research Foundation, Ithaca, NY (US); Clinical Research Institute of Montreal, Montreal, Quebec (CA)

( * ) Notice: Subject to any disclaimer, the term of this patent is extended or adjusted under 35 U.S.C. 154(b) by 776 days.

This patent is subject to a terminal disclaimer.

(21) Appl. No.: 10/333,485

(22) PCT Filed: Jul. 18, 2001

(86) PCT No.: PCT/US01/22563

§ 371 (c)(1),
(2), (4) Date: Aug. 25, 2003

(87) PCT Pub. No.: WO02/05748

PCT Pub. Date: Jan. 24, 2002

(65) Prior Publication Data

US 2004/0029796 A1 Feb. 12, 2004

Related U.S. Application Data

(60) Provisional application No. 60/219,046, filed on Jul. 18, 2000.

(51) Int. Cl.
*A61K 38/00* (2006.01)
*A61K 38/08* (2006.01)
*A61K 38/12* (2006.01)

(52) U.S. Cl. .................................. 514/2; 514/9; 514/17
(58) Field of Classification Search .................. None
See application file for complete search history.

(56) References Cited

U.S. PATENT DOCUMENTS

| 5,312,899 A | 5/1994 | Schiller |
| 5,602,100 A | 2/1997 | Brown et al. |
| 5,993,848 A | 11/1999 | Suzuki et al. |
| 6,703,483 B1 | 3/2004 | Schiller |
| 6,900,178 B2 * | 5/2005 | Oeltgen et al. ............. 514/13 |

FOREIGN PATENT DOCUMENTS

| CA | 2361364 | 9/2000 |
| WO | WO95/22557 | 8/1995 |
| WO | WO 00/55189 | 9/2000 |

OTHER PUBLICATIONS

Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Zhao et al. J Pharmacol Exp Ther. 2002; 302: 188-196.*
Lishmanov et al. Life Sciences. 1999; 65: PL 13-17.*
Demas et al. Br J Anaesth. 1986; 58: 1357-1564.*
Shroff et al. J. Clin Anesthesia. 1997; 9: 415-419.*
Lasukova et al., Patol Fiziol Eksp Ter. 2001 2: Abstract Only; article in Russian.*
Song et al. Coron Artery Dis. 2005; 16: 407-410.*
Schiller et al. Eur J Med Chem. Oct. 2000; 35: 895-901.*
Clapp III, et al. "Cardiovascular and Metabolic Responses to Two Receptor-Selective Opioid Agonists in Pregnant Sheep", Am. J. Obstet. Gynecol., vol. 178, No. 2 (Feb. 1998) pp. 397-401.
Holsey, et al. "Cardiovascular Effects of a µ-Selective Opioid Agonist (Tyrosine-D-Arginine-Phenylalanine-Lysine-$NH_2$) in Fetal Sheep: Sites and Mechanisms of Action", Am. J. Obstet. Gynecol., vol. 180, No. 5 (May 1999) pp. 1127-1130.
Kett, et al. "Baroreflex-Mediated Bradycardia but Not Tachycardia is Blunted Peripherally by Intravenous µ-opioid Agonists", Am. J. Obstet. Gynecol., vol. 178, No. 5 (May 1998) pp. 950-955.
Neilan, et al. "Pharmacological Characterization of the Dermorphin Analog [$Dmt^1$]DALDA, a Highly Potent and Selective µ-Opioid Peptide", European Journal of Pharmacology, vol. 419, Issue 1 (2001) 15-23.
Omoniyi, et al. "A Peripheral Site of Action for the Attenuation of Baroreflex-Mediated Bradycardia by Intravenous µ-Opioid Agonists", Journal of Cardiovascular Pharmacology™, vol. 35, No. 2 (2000) pp. 269-274.
Schiller, et al. "Dermorphin Analogues Carrying an Increased Positive Net Charge in Their "Message" Domain Display Extremely High µ Opioid Receptor Selectively", Journal of Medicinal Chemistry, vol. 32, No. 3 (1989) pp. 698-703.
Schiller, et al. "Synthesis and In Vitro Opioid Activity Profiles of DALDA Analogues", European Journal of Medicinal Chemistry, vol. 35, Issue 10 (Oct. 2000) pp. 895-901.
Shimoyama, et al. "Antinociceptive and Respiratory Effects of Intrathecal H-Tyr-D-Arg-Phe-Lys-$NH_2$ (DALDA) and [$Dmt^1$] DALDA", The Journal of Pharmacology and Experimental Therapeutics, vol. 297, No. 1 (Apr. 2001) pp. 364-371.

(Continued)

*Primary Examiner*—Elizabeth C. Kemmerer
*Assistant Examiner*—Christina Borgeest
(74) *Attorney, Agent, or Firm*—Hoffmann & Baron, LLP; Irving N. Feit

(57) ABSTRACT

The present invention provides methods for stimulating a mu-opioid receptor agonist peptide in a mammal in need thereof. The methods comprise administering to the mammal an effective amount of a selective mu-opioid receptor agonist peptide that comprises at least two α-amino acid residues. At least one of the amino acid residues has a positive charge. The amino acid residue in the first position is a tyrosine or tyrosine derivative. The amino acid in the second position is a D-α-amino acid. The present invention also provides methods of treating a mammal suffering from conditions or diseases by administering to the mammal an effective amount of the peptides.

4 Claims, 6 Drawing Sheets

OTHER PUBLICATIONS

Szeto, et al. "In Vivo Disposition of Dermorphin Analog (DALDA) in Nonpregnant and Pregnant Sheep", The Journal of Pharmacology and Experimental Therapeutics, vol. 284, No. 1 (1998) pp. 61-65.

Szeto et al. "Respiratory Depression After Intravenous Administration of σ-Selective Opioid Peptide Analogs", Peptides, vol. 20 (1999) pp. 101-105.

Szeto, et al. "Mu-Opioid Receptor Densensitization and Resensitization In Vivo", International Narcotics Research Conference, Poster Abstracts, Monday (1999) Mon19, p. 5.

Szeto, et al. "In Vivo Pharmacokinetics of Selective μ-Opioid Peptide Agonists", The Journal of Pharmacology and Experimental Therapeutics, vol. 298, No. 1 (Jul. 2001) pp. 57-61.

Wu, et al. "Myocardial Protective Effect of Mu Opioid Agonists", International Narcotics Research Conference, Poster Abstracts, Sunday (1999) Sun59, p. 15.

Zadina et al., "A Potent and Selective endogenous Agonist for the μ-Opiate Receptor", *Nature*, vol. 386, pp. 499-502(1997).

Spetea, et al., "Interaction of Agonist Peptide [$^3$H] Try-D-Ala-Phe-Phe-NH$_2$ with μ-Opioid Receptor in Rat Brain and CHO-μ/1 Cell Line", *Peptides*, vol. 19, No. 6, pp. 1091-1098 (1998).

Dooley et al., "Selective Ligands for the μ,σ, and κ Opioid Receptors Identified from a Single Mixture Based Tetrapeptide Positional Scanning Combinatorial Library", *Journal of Biological Chemistry*, vol. 273, No. 30, pp. 18848-18856 (1998).

Schiller et al., "Opioid Peptide Analogs with Novel Activity Profiles as Potential Therapeutic Agents for Use in Analgesia", *Pept. Sci*, Present Future, Proc. Int. Pept. Symp., 1$^{st}$, pp. 665-669 (1999).

Herve et al., "On the Immunogenic Properties of Retro-Inverso Peptides. Total Retro-Inversion of T-Cell Epitopes Causes a Loss of Binding to MHC II Molecules". Molecular Immunology, vol. 34, No. 2, pp. 157-163 (1997).

Guerrini, et al., "Opioid receptor selectivity alteration by single residue replacement: synthesis and activity profile of [Dmt] deltorphin B", European Journal of Pharmacology 302, (1996) 37-42. Abstract only.

James A Wells, "Additivity of Mutational Effects in Proteins", Biochemistry, American Chemical Society, vol. 29, No. 37, Sep. 18, 1990.

Ngo, et al., "Computational Complexity, Protein Structure Prediction, and the Levinthal Paradox", The Protein Folding Problem and Tertiary Structure Prediction, K. Merz, Jr. and S. Le Grand, Editors, Birkhauser Boston, 1994.

* cited by examiner

MEDICINAL USES OF MU-OPIOID RECEPTOR AGONISTS

This application claims priority from U.S. provisional application Ser. No. 60/219,046 filed Jul. 18, 2000, the contents of which are incorporated herein by reference.

This invention was made with Government support from the National Institute on Drug Abuse under Grant No. P01 DA08924. The Government has certain rights in this invention.

The invention as claimed herein was made pursuant to a joint research agreement, within the meaning of 35 U.S.C. § 103(c) between Cornell Research Foundation, Inc. and Institut de Recherches Cliniques de Montreal. The joint research agreement was in effect on or before the date the claimed invention was made, and the claimed invention was made as a result of activities undertaken within the scope of the joint research agreement.

BACKGROUND OF THE INVENTION

Opiates (derived from the opium poppy) or opiate-like (synthetic) drugs are widely used to alleviate moderate to severe pain. These drugs are classified together as opioids. Opioids derived from the opium poppy include morphine and codeine. Opiate-like or synthetic drugs include fentanyl, meperidine and methadone.

Opioids bind to specific receptor molecules. Distinct categories of opioid receptors have been identified which include mu, delta and kappa receptors. (W. Martin et al., J. Pharmacol. Exp. Ther. 197, 517 (1977)).

Opioids are useful for various kinds of pain management. In particular, opioids are used to alleviate postoperative pain and chronic pain, such as cancer and neuropathic pain, and pain during labor and delivery. However, opioid use has been linked to many dangerous side effects, such as tolerance or physical dependence, constipation, cardiac depression and respiratory depression.

One major concern with opioid use has been the transfer of opioids across the placenta to the fetus. Opioids may adversely affect the fetus by compromising the delivery of oxygen and substrates from the mother. The respiratory depressant effects of opioids may also decrease fetal oxygen availability.

Another concern with the currently available opioids is that they are too short-acting for labor pain. For example, fentanyl usually provides relief for only 60 to 90 minutes. Labor pain can last up to twelve hours.

In addition, due to the depression of cardiac and respiratory function seen with opioids, dangers exist when opioids are used before and during surgery when the patient has compromised cardio-respiratory functions. For example, respiratory depression is especially risky for individuals who have compromised respiratory systems, such as asthmatics and smokers Opioids negatively affect motor function and are also associated with undesirable sedative effects. This is problematic for orthopedic and joint replacement surgeries, which require immediate post-operative motility.

Accordingly, there is a need for pain management treatments that do not depress cardiac or respiratory function and do not affect motor function.

Further, there is a need for new pain management treatments that do not cross the placental barrier or compromise the maternal respiratory and cardiac function. In addition, longer acting treatments for pain are needed.

Additionally, it would be beneficial to have a pain management treatment that will be effective in mammals that have developed a tolerance to opioids.

SUMMARY OF THE INVENTION

The present invention is directed to a method for stimulating a mu-opioid receptor in a mammal in need thereof. The method comprises administering systemically to the mammal an effective amount of a selective mu-opioid receptor agonist peptide. The peptide comprises at least two α-amino acid residues, at least one α-amino acid residue having a positive charge. The α-amino acid residue in the first position is tyrosine or a tyrosine derivative, and the α-amino acid residue in the second position is a D-α-amino acid.

In an additional embodiment, the present invention is directed to a method for stimulating a mu-opioid receptor in a mammal in need thereof. The method comprises administering intrathecally or orally to the mammal an effective amount of a selective mu-opioid receptor agonist peptide selected from the group consisting of 2',6'-dimethyl-Tyr-D-Arg-Phe-Lys-NH$_2$, Tyr-D-Ala-Phe-Phe, 2',6'-dimethyl-Tyr-Ala-Phe-Phe-NH$_2$ and 2',6'-dimethyl-Tyr-D-Arg-Phe-Orn-NH$_2$.

Another embodiment of the invention is directed to a method for reducing pain in a mammal in need thereof without risk of respiratory depression. The method comprises administering to the mammal an effective amount of a selective mu-opioid receptor agonist peptide selected from the group consisting of 2', 6'-dimethyl-Tyr-D-Arg-Phe-Lys-NH$_2$, Tyr-D-Ala-Phe-Phe, 2', 6'-dimethyl-Tyr-D-Ala-Phe-Phe-NH$_2$ and 2', 6'-dimethyl-Tyr-D-Arg-Phe-Orn-NH$_2$.

Another embodiment of the invention is a method for protecting a mammal's heart from ischemic-reperfusion injury before, during and/or after cardiac surgery. The method comprises administering to the mammal an effective amount of a selective mu-opioid receptor agonist peptide. The peptide comprises at least two α-amino acid residues with at least one α-amino acid residue having a positive charge. The α-amino acid residue in the first position is a tyrosine or tyrosine derivative and the α-amino acid residue in the second position is a D-α-amino acid.

In yet another embodiment of the invention, is a method for inhibiting norepinephrine uptake in a mammal in need thereof. The method comprises administering an effective amount of a selective mu-opioid receptor agonist peptide. The peptide comprises at least two α-amino acid residues with at least one α-amino acid residue having a positive charge. The α-amino acid residue in the first position is a tyrosine or tyrosine derivative and the α-amino acid residue in the second position is a D-α-amino acid.

In a final embodiment of the invention, is a method for treating cardiac failure or angina in a mammal in need thereof. The method comprises administering an effective amount of a selective mu-opioid receptor agonist peptide. The peptide comprises at least two α-amino acid residues with at least one α-amino acid residue having a positive charge. The α-amino acid residue in the first position is a tyrosine or tyrosine derivative and the α-amino acid residue in the second position is a D-α-amino acid.

DETAILED DESCRIPTION

Figure 1:
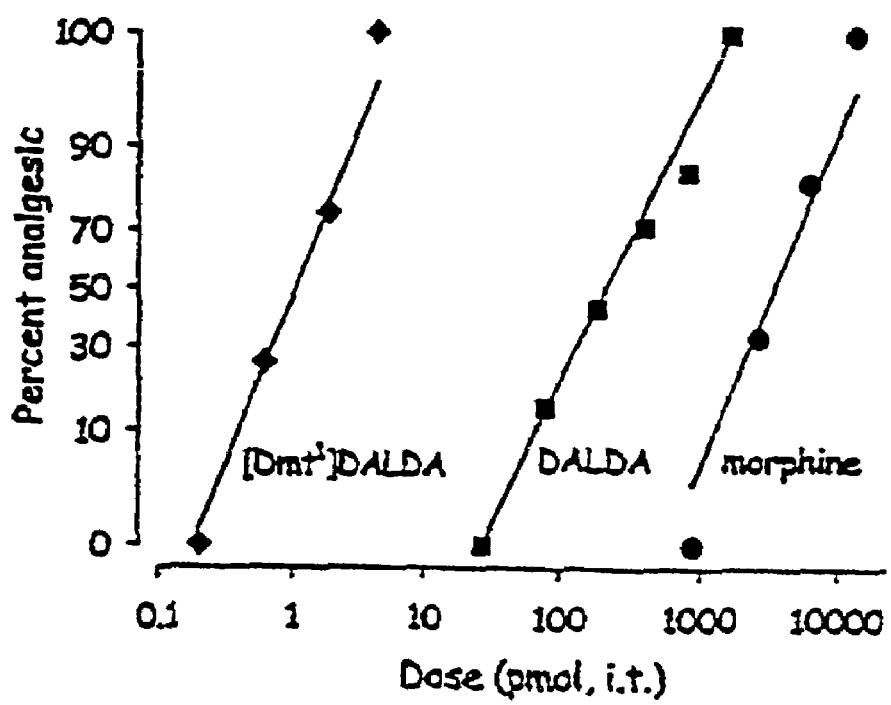
FIG. 1. Dose-dependent antinociceptive effects of intrathecal MOR, DALDA, and [Dmt$^1$]DALDA in the tail-flick test (n=10 in each group).

It has now been discovered that certain selective mu-opioid receptor agonist peptides can be used for pain management. The peptides have fewer of the dangerous side effects associated with conventional opioids.

The peptide comprises at least two α-amino acid residues. In this specification, an α-amino acid residues may be any naturally occurring or non-naturally occurring D or L α-amino acid. The naturally occurring amino acids are typically the twenty most common amino acids, i.e. alanine (ala), arginine (arg), asparagine (asn), aspartic acid (asp), cysteine (cys), glutamine (glu), glutamic acid (glu), glycine (gly), histidine (his), isoleucine (ileu), leucine (leu), lysine (lys), methioine (met), phenylalanine (phe), proline (pro), serine (ser), threonine (thr), tryptophan, Trp), tyrosine (tyr), and valine (val).

The non-naturally occurring amino acids can be any organic molecule which contains an amino acid group. For example, the non-naturally occurring amino acids may be a derivative of a naturally occurring amino acid. Some examples of non-naturally occurring α-amino acids include homolysine, 2,3 or 2,4-diaminobutyric acid, 2,3-diaminopropionic acid, ornithine, norleucine, and norvaline.

The residue at first position of the peptide, i.e. the N-terminal position, is tyrosine or, preferably, a derivative of tyrosine. A derivative of tyrosine is a tyrosine with one or more structural modifications. Structural modifications to tyrosine include, for example, the addition of one or more groups to the benzene ring or to the amino group.

For example, one or more groups can be added to one or more of the 2', 3', 5', or 6' position of the benzene ring. The group can be any group that can be added to a benzene ring. Some examples of such groups include hydroxy, $C_1$-$C_4$ alkoxy, amino, methylamino, dimethlyamino, nitro, halo (fluoro, chloro, bromo, or iodo), or branched or unbranched $C_1$-$C_4$ alkyl, such as methyl, ethyl, n-propyl, isopropyl, butyl, isobutyl, or t-butyl.

Some examples of groups that can be added to the amino group of tyrosine include the $C_1$-$C_4$ alkyl groups mentioned above. Preferred derivatives of tyrosine include 2'-methyltyrosine (mmt), 2',6'-dimethyltyrosine (dmt), N,2',6'-trimethyltyrosine (tmt) and 2'-hydroxy-6'-methyltyrosine (hmt).

The α-amino acid residue in the second position of the peptide is a D-α-amino acid. The D-α-amino acid may be any naturally occurring or non-naturally occurring D α-amino acid. The remaining amino acid residues can be any naturally or non-naturally occurring D or L-α-amino acid residues.

The peptide preferably comprises no more than seven amino acid residues. More preferably, the peptide comprises no more than five amino acid residues. Most preferably, the peptide comprises four amino acid residues.

The peptide may be a linear peptide. Alternatively, the peptide is a cyclic peptide. In a cyclic peptide, a first group, preferably a carboxyl group, forms a covalent bond with a second group, preferably an amino group. The first group is preferably on the C-terminal amino acid. The second group is preferably on the N-terminal amino acid.

The mu-opioid receptor peptide of the present invention has at least one α-amino acid residue that has a positive charge at physiological pH. Preferably at least two or three α-amino acid residues have a positive charge at physiological pH. Some examples of α-amino acid residues that have a positive charge at physiological pH include tyrosine and tyrosine derivatives, arginine, lysine, histidine, 2,3- or 2,4- diaminobutyric acid, and 2,3-diaminopropionic acid.

In a preferred embodiment, the C-terminal residue of the peptide is an amide derivative of the carboxylate group. The amide group may be, for example, amido, N-methylamido, N-ethylamido, N,N-dimethylamido, or N,N-diethylamido.

Some examples of peptides include H-Tyr-D-Arg-Phe-Lys-$NH_2$ (DALDA) and 2',6'-dimethyl-Tyr-D-Arg-Phe-Lys-$NH_2$ ((dmt[1])DALDA). Examples of other peptides include Tyr-D-Ala-Phe-Phe (TAPP), 2',6'-dimethyl-Tyr-D-Ala-Phe-Phe-$NH_2$, and 2',6'-dimnethyl-Tyr-D-Arg-Phe-Orn-$NH_2$. (An —$NH_2$ after the C-terminal amino acid residue indicates an amide group.)

In one embodiment, the invention relates to a method for stimulating a mu-opioid receptor in a mammal. The method comprises administering to the mammal an effective amount of any selective mu-opioid receptor agonist peptide described above. In this embodiment, the peptide is administered systemically. In this specification, systemic administration means intravenous, subcutaneous, or intramuscular administration.

In view of prior art teachings to the contrary, see Clapp et al, Am. J. Obstet. Gynecol. 178, 397-401 (199w), it is e that the peptides are effective when administered systemically. Clapp et al, teach that mu-opioid selective agonist peptides like those of the present invention are not expected to produce sufficient analgesia when administered systemically.

In another embodiment, the method relates to a method for stimulating a mu-opioid receptor in a mammal comprising administering intrathecally or orally to the mammal an effective amount of a selective mu-opioid receptor agonist peptide. The peptide is selected from the group consisting of 2',6'- dimethyl-Tyr-D-Arg-Phe-Lys-NH$_2$, Tyr-D-Ala-Phe-Phe, 2',6'-dimethyl-Tyr-D-Ala-Phe-Phe-NH$_2$ and 2',6'-dimethyl-Tyr-DArg-Phe-Orn-NH$_2$.

In another embodiment the invention relates to a method for reducing pain in a mammal without risk of respiratory depression. Respiratory depression refers to a decrease in the rate and depth of respiration. The method comprises administering to the mammal an effective amount of a selective mu-opioid receptor agonist peptide. The peptide is selected from the group consisting of 2',6'-dimethyl-Tyr-D-Arg-Phe-Lys-NH$_2$, Tyr-D-Ala-Phe-Phe, 2',6'-dimnethyl-Tyr-D-Ala-Phe-Phe-NH$_2$ and 2',6'-dimethyl-Tyr-D -Arg-Phe-Orn-NH$_2$. The peptide may be administered by any mode of administration. Systemic, intrathecal, or oral administration is preferred.

In another advantage, administration of the peptides of the present invention is not accompanied by constipation.

A disadvantage of the opioids of the prior art is that they have the ability to cross the placental barrier and cause adverse effects in a fetus. For example, neonatal respiratory depression and changes in the neurobehavior of a child have been associated with the use of opioids during labor and delivery when the opioids are transferred across the placenta.

One advantage of the peptides of the present invention is their limited ability to cross the placental barrier. Accordingly, the peptides of the present invention avoid the undesirable side effects mentioned above.

A major advantage of the methods of the invention is that they are useful in mammals already tolerant to opioids. Tolerance to opioids refers to a decrease in the effects of an opioid at its previous dose, or the need for a higher dose to maintain the same effect. Cross-tolerance is a phenomenon where an individual who has developed tolerance to one opioid, usually is tolerant to other opioids.

The peptides used in the methods of the present invention do not exhibit cross-tolerance. Accordingly, the peptides are effective in an individual who has developed tolerance to other opioids, but remains in need of pain reduction. This situation may, for example, occur in individuals who suffer from chronic pain, such as pain from cancer or neuropathic pain. Neuropathic pain refers to pain that results from a disturbance of function or pathologic change in the nervous system, including the central nervous system and peripheral nervous system.

For these and other reasons, the peptides of the invention are effective as analgesic or anesthetic agents. For example, the peptides are suitable for treating pain caused by surgery. The peptides may be administered before, during, or after surgery. The method is useful in any type of surgery including cardiac surgery, joint replacement surgery or transplantation surgery.

In addition to their analgesic properties, the peptides of the present invention have been shown to improve myocardial contractile force and cardiac performance. Accordingly, the peptides of the invention are particularly useful in mammals that suffer from painful conditions, and are also in need of improving myocardial contractile force or cardiac performance.

For example, the peptides are useful for preconditioning and protecting a heart before and/or during cardiac surgical procedures. Such procedures include, for example, coronary bypass and angioplasty. The peptides of the present invention can be given prior to or during cardiac surgery to precondition the heart, to protect it against ischemic damage, and/or to relieve pain.

Moreover, the peptides can be given before, during and/or after cardiac surgery, such as coronary bypass, to provide both pain relief and protection against myocardial ischemia-reperfusion injury. After a myocardial ischemic episode, an immediate goal is to reperfuse the heart muscles, i.e. restoring blood flow to the heart. Early reperfusion, after an ischernic episode, minimizes the extent of heart muscle damage and preserves the pumping function of the heart. By improving myocardial contractile force, the peptides of the invention can facilitate reperfusion after an ischemic episode.

The method of the present invention is beneficial at any other time a mammal is in need of improving myocardial contractile force or cardiac performance of a heart. Such need occurs, for example, in cardiac failure and angina. Angina refers to a temporary chest pain that is caused by insufficient blood reaching the heart, i.e. myocardial ischemnia. The method is particularly useful if the mammal also requires relief of pain.

Accordingly, the present invention also provides a method for treating cardiac failure or angina in a mammal in need thereof. The method comprises administering an effective amount of a selective mu-opioid receptor agonist peptide described above to the mammal. The peptide is preferably selected from the group consisting of Tyr-D-Agr-Phe-Lys-NH$_2$, 2',6'-dimethyl-Tyr-D-Arg-Phe-Lys-NH$_2$, Tyr-D-Ala-Phe-Phe, 2',6'-dimethyl-Tyr-D-Ala-Phe-Phe-NH$_2$ and 2',6'-dimethyl-Tyr-D-Arg-Phe-Orn-NH$_2$. Any mode of administration may be employed. Systemic, oral or intrathecal administration is preferred.

The peptides of the invention are also useful before, during, and after cardiac transplantation. During cardiac transplantation, a heart is removed from a donor and is transplanted into a recipient.

The cardiac performance of the heart being transplanted is improved by treating either or both of the donor and recipient in vivo with an effective amount of a peptide of the invention. Tyr-D-Arg-Phe-Lys-NH$_2$, 2',6'-dimethyl-Tyr-D-Arg-Phe-Lys-NH$_2$, Tyr-D-Ala-Phe-Phe, 2',6'-dimethyl-Tyr-D-Ala-Phe-Phe-NH$_2$ and 2',6'-dimethyl-Tyr-D-Arg-Phe-Orn-NH$_2$ are preferred.

In addition, maintenance of the heart is improved after it has been removed from the donor, and before it is transferred to the recipient, by treating the heart ex vivo with a solution of the same peptides described above for iii vivo treatment.

The peptides of the present invention are also particularly useful for treating pain before, during and after orthopedic surgery, including joint replacement surgery (hip, knee, shoulder, etc.). After orthopedic surgery, patients are encouraged to begin rehabilitation as quickly as possible. The sedative effects on motor function associated with opioids of the prior art make immediate physical rehabilitation after surgical procedures difficult.

The peptides described above do not affect motor function as drastically as the opioids of the prior art. Therefore, the peptides of the present invention permit earlier physical rehabilitation of the patient.

A further advantage of the present invention is that the peptides do not cause uterine contraction. Controlling the rate and intensity of uterine contractions during labor and delivery is an important aspect of obstetric medicine. It is undesirable to produce unwanted uterine contractions during pregnancy. Therefore, the claimed method is useful for relieving pain in pregnant women, including during labor and delivery.

In addition, it has surprisingly been discovered that the peptides of the invention inhibit norepinephrine uptake. Norepinephrine inhibition occurs particularly in spinal cord synaptasomes when the peptides are administered intrathecally Accordingly, in a final embodiment, the invention relates to a method for inhibiting norepinephrine uptake. The method comprises administering an effective amount of a peptide of the present invention to a mammal in need thereof. Preferably the peptide is Tyr-D-Arg-Phe-Lys-NH$_2$, 2',6'-dimethyl-Tyr-D-Arg-Phe-Lys-NH$_2$, Tyr-DAla-Phe-Phe, 2',6'-dimethyl-Tyr-D-Ala-Phe-Phe-NH$_2$ and 2',6'-dimethyl-Tyr-D-ArgPhe-Orn-NH$_2$. The peptides can be administered via any mode of administration, including systemic, oral and intrathecal administration.

An effective amount of the peptide will vary with the group of patients (age, sex, weight, etc.), the nature and severity of the condition to be treated, the particular polypeptide administered, and its route of administration, as is well known in the art. See the examples below for amounts administered to animals. Amounts suitable for administration to humans are routinely determined by physicians and clinicians during clinical trials.

While not being bound by theory or any particular mechanism, applicants believe that the extraordinary analgesic potency of the peptides of the present invention may be due to the combination of mu-opioid agonism and enhancement of endogenous extraneuronal norepinephrine levels resulting from the inhibition of norepinephrine uptake.

Any dosage form known in the art of pharmacy is suitable. For oral administration, liquid or solid dosage forms may be used. Some examples of dosage forms include tablets, gelatin capsules, pills, troches, elixirs, suspensions, syrups, wafers, chewing gum and the like. The peptides can be mixed with a suitable pharmaceutical carrier (vehicle) or excipient as understood by practitioners in the art. Examples of carriers and excipients include starch, milk, sugar, certain types of clay, gelatin, stearic acid or salts thereof, magnesium or calcium stearate, talc, vegetable fats or oils, gums and glycols.

For systemic or intrathecal administration, formulations of the peptides may utilize conventional diluents, carriers, etc., such as are known in the art can be employed to deliver the peptides. The formulations may comprise one or more of the following: a stabilizer, a surfactant, preferably a nonionic surfactant, and optionally a salt and/or a buffering agent. The peptide may be delivered in the form of an aqueous solution, or in a lyophilized form.

The stabilizer may, for example, be an amino acid, such as for instance, glycine; or an oligosaccharide, such as for example, sucrose, tetralose, lactose or a dextram. Alternatively, the stabilizer may be a sugar alcohol, such as for instance, mannitol; or a combination thereof. Preferably the stabilizer or combination of stabilizers constitutes from about 0.1% to about 10% weight for weight of the proneurotrophin.

The surfactant is preferably a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. Preferably, the buffering agent maintains the pH of the pharmaceutical composition in the range of about 5.5 to about 7.5. The salt and/or buffering agent is also useful to maintain the osmolality at a level suitable for administration to a human or an animal. Preferably the salt or buffering agent is present at a roughly isotonic concentration of about 150 mM to about 300 mM.

The formulations of the peptides of the present invention may additionally contain one or more conventional additive. Some examples of such additives include a solubilizer such as for example, glycerol; an antioxidant such as for example, benzalkonium chloride (a mixture of quaternary ammonium compounds, known as "quats"), benzyl alcohol, chlorotene or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The peptide may be administered via rapid intravenous bolus injection. Preferably, however, the peptide is administered as a constant rate intravenous infusion. The peptides of the invention may be administered to mammals by sustained release, as is known in the art. Sustained release administration is a method of drug delivery to achieve a certain level of the drug over a particular period of time. The level typically is measured by serum concentration.

The mammal can be any mammal, including, for example, farm animals, such as sheep, pigs, cows, and horses; pet animals, such as dogs and cats; laboratory animals, such as rats, mice and rabbits, and humans. In view of the limited ability of the peptides to cross the placental barrier, the method is especially effective for pregnant females, especially pregnant women.

EXAMPLES

Example 1

Experimental Methods for Determining Analgesic Potency and Respiratory Effects of DALDA and [Dmt[1]]DALDA After Intrathecal Administration in Rats Animals Male Sprague-Dawley Rats (300-350 g) were used.

Drugs and Drug Administration

[Dmt[1]]DALDA and DALDA are synthesized by methods known in the art. See, for example, Brown, et al, U.S. Pat. No. 5,602,100 and Schiller et al, J. Med. Chem, 32, 698703 (1989). Naloxone hydrochloride was obtained from Sigma, St. Louis, Mo. Each drug was dissolved in saline. Intrathecal delivery was performed either by direct injection or via an intrathecal catheter depending on the study.

1) Direct Percutaneous Injection.

Under light halothane anesthesia a needle connected to a Hamilton syringe was inserted percutaneously between spinal processes of the third and fourth lumbar vertebrae into the intrathecal space. A quick flick of the tail was observed when the tip of the needle entered the intrathecal space and was used as an indicator of successful puncture (Mestre et al., 1994). Drugs were delivered in a volume of 5 μl.

2) Via Intrathecal Catheter

Intrathecal catheterization was performed at least two days prior to the experiment as previously described (Shiinoyama, N. et al., 1996). Briefly, under halothane anesthesia, a PE-10 tube was inserted through a small hole made in the atlanto-occipital membrane and threaded 8.5 cm down the intrathecal space to the lumbosacral level of the spinal cord. Drugs were delivered via the catheter in a volume of 5 μl, followed by 10 μl saline to flush the catheter.

Example 2

Analgesic Testing

To assess the antinociceptive effects of the opioids, the tail-flick test was used. Radiant heat was applied to the tail at 5-8 cm from the tip using a tail-flick apparatus (IITC, Woodland Hills, Calif.). The time from the onset of the heat to the withdrawal of the tail (tail-flick latency) was measured. The intensity of the radiant heat was adjusted so that baseline latencies would fall between 2.5 and 3.5 seconds. To avoid tissue damage the heat stimulus was discontinued after seven seconds. A baseline latency was obtained for each animal prior to the administration of any drug. Subsequent response latencies were determined at designated time points. Analgesic testing was performed by a blinded investigator.

Study 1. Analgesic Potencies of Intratliecal Morphine ("MOR"), DALDA and [Dmt$^1$]DALDA Cumulative dose-response studies were performed for each drug using the tail-flick test (Shimoyama, N. et al., 1996, Shimoyama, N. et al., 1997). Each drug was tested in a group of ten rats. After measuring the baseline latencies, increasing doses of each drug were administered via an intrathecal catheter until each animal in the group became an analgesic responder. An analgesic responder was defined as one whose response tail-flick latency was two or more times the value of the baseline latency. The response latency after each dosing was determined at peal analgesia, which was 15, 30 and 45 min after the administration of the MOR, DALDA and [Dmt$^1$]DALDA, respectively (based on preliminary studies). Any subsequent dosing was performed immediately after the determination of response latency. The percentage of analgesic responders in the group of rats for each cumulative dose was calculated, and a cumulative dose-response curve was constructed. The dose-response data were analyzed by the BLISS-21 computer program. This program maximized the log-likelihood function to fit a parallel set of gaussian normal sigmoid curves to the dose-response data and provides $ED_{50}$ values, 95% confidence interval (CI) and relative potency estimates (Umans and Inturrisi, 1981).

MOR, DALDA, and [Dmt$^1$]DALDA each produced a dose-dependent antinociceptive effect in the tail-flick test (FIG. 1). $ED_{50}$ values and potency ratios obtained from the quantal dose-response curves are shown in Table 1. DALDA was 14 times more potent than MOR, whereas [Dmt$^1$]DALDA showed a 3000-fold greater potency compared with MOR.

TABLE 1

$ED_{50}$ values and relative potencies of the antinociceptive effects of intrathecal MOR, DALDA, and [Dmt$^1$]DALDA in the rat tail-flick test

| Compound | $EDT_{50}$ pmol | 95% CI | Potency Ratios |
|---|---|---|---|
| Morphine | 3330 | 1940-5600 | 1 |
| DALDA | 237 | 149-370 | 14.1 |
| [Dmt$^1$]DALDA | 1.06 | 0.64-1.71 | 3160 |

Study 2. Naloxone Reversal of Antinociceptive Effects

The effect of naloxone on the antinociceptive effects of intrathecal MOR, DALDA and [Dmt$^1$]DALDA was examined. An equipotent dose (3 times the $ED_{50}$ value determined in Study 1) of MOR, DALDA or [Dmt$^1$]DALDA was given via an intrathecal catheter. Tail-flick latencies were measured prior to the administration of any drug and at the time of peak analgesia for each compound (at 15, 30 and 45 minutes after administration, for MOR, DALDA and [Dmt$^1$]DALDA, respectively). Naloxone hydrochloride at a dose of 82.5 nmol or saline was administered via the intrathecal catheter 10 minutes prior to the second tail-flick testing. Four rats were tested for each combination of drugs. Data were analyzed using the paired t-test.

In rats that received MOR, DALDA, or [Dmt$^1$]DALDA followed by saline, all tail-flick latencies reached cut-off (7 s) at the time of peak effect of each agonist. When naloxone (82.5 mnol) was administered instead of saline, the tail-flick latencies measured at the time of peak effect were not different from baseline values (Table 2).

A dose 3 times the $ED_{50}$ value of MOR, DALDA, or [Dmt$^1$]DALD)A was administered intrathecally. Tail-flick latencies were measured prior to the administration of any drug (=baseline latency) and at the time of peak analgesia (=response latency). Nalaxone hydrochloride at 82.5 nmol or saline was administered intrathecally 10 min prior to the second tail-flick measurement (n=4 for each group). The results are shown in Table 2.

TABLE 2

Reversal of antinociceptive effects of MOR, DALDA, and [Dmt$^1$]DALDA by nalozone

| Compounds | Baseline Latencies | Response Latencies |
|---|---|---|
| MOR + saline | 2.78 ± 0.50 | 7 (cut-off latency)* |
| DALDA + saline | 2.63 ± 0.15 | 7 (cut-off latency)* |
| [Dmt$^1$]DALDA + saline | 2.83 ± 0.17 | 7 (cut-off latency)* |
| MOR + naloxone | 3.08 ± 0.31 | 3.13 ± 0.41 |
| DALDA + naloxone | 2.65 ± 0.17 | 2.90 ± 0.43 |
| [Dmt$^1$]DALDA + naloxone | 2.88 ± 0.10 | 2.68 ± 0.15 |

*Significantly different tram baseline ($p < 0.05$).

Study 3. Time Course of Antinociceptive Effects

Equipotent doses (3 times the $ED_{50}$ value obtained in Study 1) of MOR, DALDA and [Dmt$^1$]DALDA were given intrathecally by direct percutaneous injection. Tail-flick latencies were measured prior to and every hour up to 15 hours after the administration of each drug. The number of rats tested for each drug was 8. Data were analyzed using the one-way analysis of variance followed by the Dunnett's test.

Figure 2:
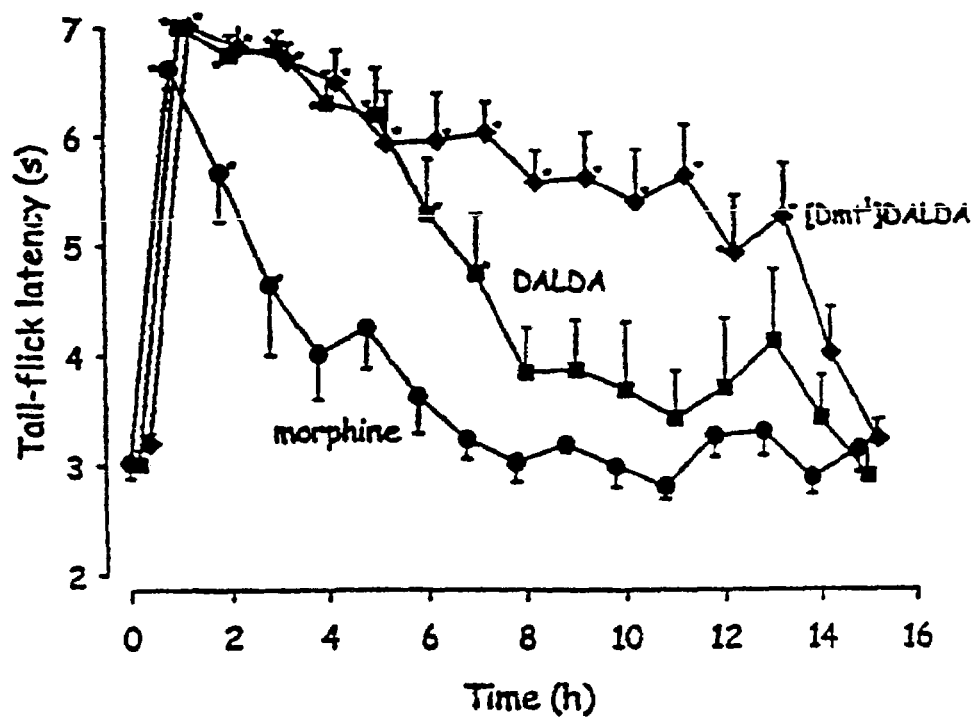
FIG. 2. Time course of antinociceptive effects of intrathecal MOR, DALDA, and [Dmt[1]]DALDA. A dose of 3 times the $ED_{50}$ value was given. Tail-flick latencies were measured before and every hour up to 15 h after the administration of the drug (n=8 in each group). *Significantly different from baseline values (p<0.05).

As shown in FIG. 2, MOR, DALDA, and [Dmt$^1$]DALDA showed different time courses of antinociceptive effects after intrathecal administration of equipotent doses of the three drugs (3 times the $ED_{50}$ value for antinociceptive effect). The tail-flick latencies were significantly greater than baseline for 3, 7, and 13 h after the intrathecal administration of MOR, DALDA, and [Dmt$^1$]DALDA, respectively. All tail-flick latencies returned to baseline by the end of the experiment.

Study 4. Respiratory Effects of Intiathecal MOR, DALDA and [Dmt$^1$]DALDA

The effects of each drug on minute ventilation (VE) under 5% $CO_2$ challenge were evaluated using whole body plethysmography (Tatsumi et al., 1991). An unrestrained rat was placed in a 3-liter whole-body plethysmograph chamber. After a 15 min acclimation period, a gas mixture of 5% $CO_2$ and 21% $O_2$ in $N_2$ (100% humidified) was supplied into and out of the chamber at a rate of 1000 mi/min, and the animal was allowed to breathe the gas mixture for 5 minutes. After a steady-state ventilatory condition had been reached, with the animal awake and quiet, the inlet and outlet of the chamber were closed and the pressure changes in the box (due to the warming and wetting of the gas inspired by the rat and the cooling and drying of the expired gas) were recorded using a high-gain differential pressure transducer. A calibration volume of 0.2 ml of air was regularly introduced into the chamber during the recordings. The recordings were made for 20 to 30 seconds. Tidal volumes were calculated from the pressure changes using the equation derived by Drorbaugh and Fenn (1955). Respiratory frequencies were determined from the number of respiratory cycles in the recordings and VE values were calculated (tidal volume×frequency).

Rats were randomly assigned to one of 7 groups. The number of rats in each group was 6 to 10. The animals of each group were given 3 times (lower dose) or 30 times (higher dose) the $ED_{50}$ value (antinociceptive) of MOR, DALDA or [Dmt$^1$]DALDA, or saline by direct percutaneous intrathecal injection. VE under 5% $CO_2$ challenge was determined prior to and every hour up to 10 hours after the administration of the drug. VE values were expressed as a percentage of the baseline VE value obtained prior to the administration of any drug. The smallest VE value obtained after the administration of a drug (minimum V E) was determined for each animal. Mean values of the minimum V E for animals of each group were compared using the one-way analysis of variance followed by the Dunnett's test. For each animal, respiratory depression was defined as a minimum VE value that is below two standard deviations of the mean (mean−2×SD) of the saline group.

Figure 3:
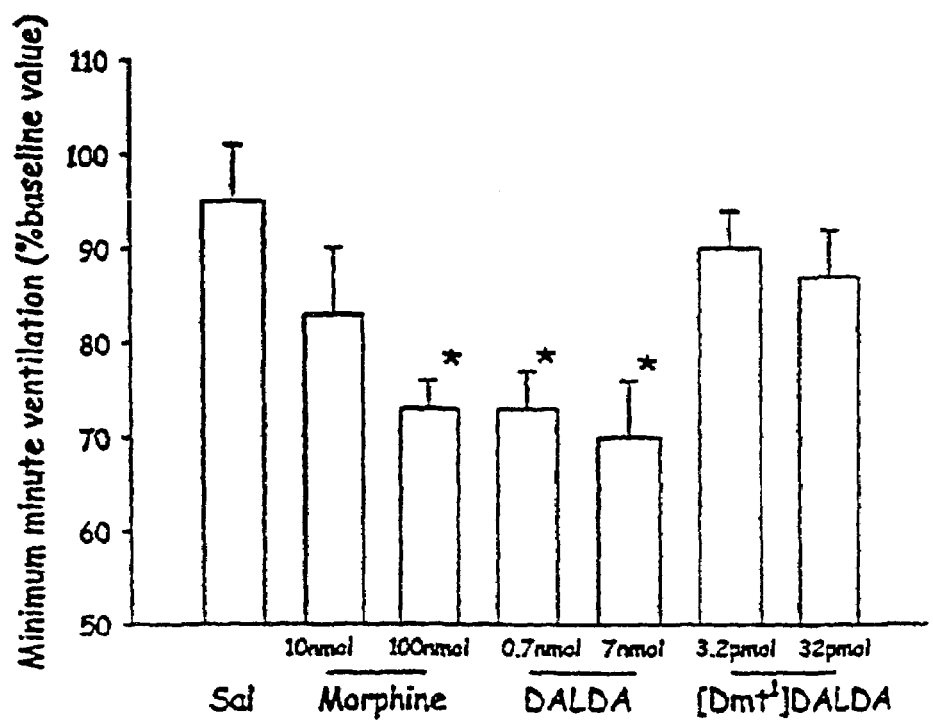
FIG. 3. Effects of intrathecal MOR, DALDA, and [Dmt[1]] DALDA on minute ventilation during hypercapnic breathing. Doses of 3 times the $ED_{50}$ value and 30 times the $ED_{50}$ value (antinociceptive effect) of each drug were administered. The smallest minute ventilation value (minimum minute ventilation) during the postadministration period was determined and expressed as percentage of baseline minute ventilation. n=6-10 in each group. *Significantly different from saline group (p<0.05).

The effects of MOR, DALDA, and [Dmt$^1$]DALDA on minimum VE are illustrated in FIG. 3. Compared with the group that received saline, the minimum VE was significantly lower in the group that received the high dose of MOR (30 times the antinociceptive $ED_{50}$) but not in the group that received the low dose of MOR (3 times the antinociceptive $ED_{50}$). Both the low- and high-dose DALDA groups showed a significantly lower minimum VE. In contrast, the minimum VE was not different in the low- or high-dose of [Dmt$^1$] DALDA. When the minimum VE of each animal was checked to determine whether it satisfied the criterion set for respiratory depression [less than a critical value of mean—(2×S.D.) of the minimum VE of the saline group], a substantial number of animals in the groups that showed a decrease in the mean value of minimum VE had a minimum VE value lower than the critical level (a "low minimum VE") (Table 4). Furthermore, one animal of the lower dose MOR group and one animal of the higher dose. [Dmt$^1$]DALDA group also had a low minimum VE, although the mean values of the groups were not significantly different from the saline group. No animal in the lower dose [Dmt$^1$]DALDA group showed a low minimum VE. The timing of the occurrence of low minimum VE for each animal was between 3 and 5 h after administration for all groups.

Doses of 3 times the $ED_{50}$ value and 30 times the $ED_{50}$ value (antinotioeptive) of each drug were administered. A minimum VE value (see Materials and Methods) less than the mean—(2×S. D.) of the minimum VE value of the saline group was considered a "low minimum VE". The results are shown in Table 3.

Study 5: Effects of $\alpha_2$-Adrenergic Blockade.

Effect of $\alpha_2$-Adrenergic Blockade on Antinociceptive Action of [Dmt$^1$]DALDA and DALDA. The antinociceptive effect of intrathecal [DMT$^1$]DALDA and DALDA were compared in the absence and presence of intrathecal yohimbine, an $\alpha_2$-adrenergic antagonist. Rats were administered [DMT$^1$] DALDA alone (1.1 pmol, n=10), [DMT$^1$]DALDA (1.1 pmol) and yohimbine (100 μg) (n=10), DALDA alone (240 pmol, n=9), DALDA (240 pmol) and yohimbine (100 μg) (n=9), or yohimbine alone (100 μg) (n=6). Due to the limited solubility of yohimbine, the drug solutions were prepared with 50% dimethyl sulfoxide in saline and delivered in a volume of 104 l. Intrathecal administration of 10 μL of 50% dimethyl sulfoxide in saline by itself did not have any effect on tail-flick latency (n=4, data not shown). Tail-flick latencies were measured before and every 20 min up to 120 min after drug administration. Within-group differences were analyzed by one-way ANOVA and between-group differences were analyzed by two-way ANOVA.

Figure 4:
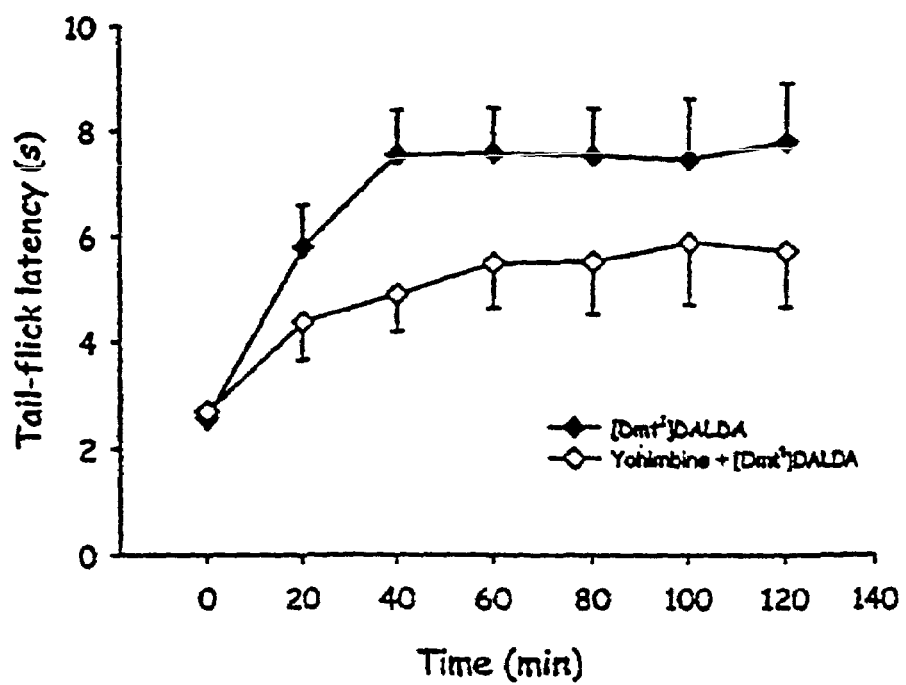
FIG. 4. Effect of yohimbine on the antinociceptive effects of [Dmtl[1]]DALDA. [Dmtl[1]]DALDA (1.1 pmol) alone, [Dmt[1]] DALDA (1.1 pmol) and yohimbine (100 μg), or yohimbine (100 μg) alone were given intrathecally to rats. Tail-flick latencies were measured before and every 20 min after drug administration. Yohimbine significantly attenuated the antinociceptive effect of [Dmt[1]]DALDA (p<0.05, two-way ANOVA) while not having any effect on tail-flick latency by itself.
Figure 5:
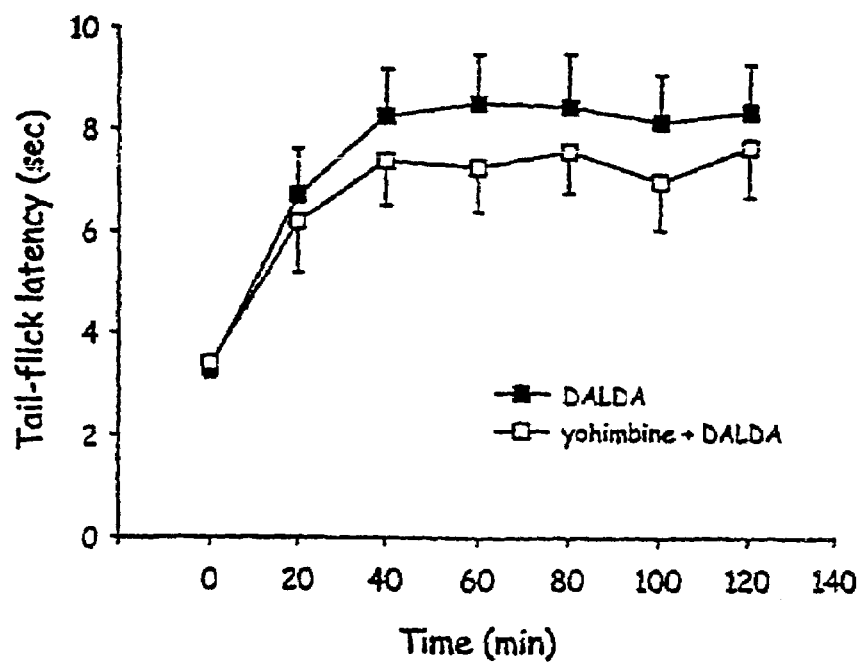
FIG. 5. Effect of yohimbine on the antinociceptive effects of DALDA. DALDA (240 pmol) alone, DALDA (240 pmol) and yohimbine (100 μg), or yohimbine (100 μg) alone were given intrathecally to rats. Tail-flick latencies were measured before and every 20 min after drug administration. The antinociceptive effect of DALDA was not significantly attenuated by yohimbine.

Yohimbine (100 μg) alone had no effect on tail-flick latency at any time compared with baseline value (data not shown). The addition of yohimbine (100 μg) significantly attenuated the antinociceptive effect of [Dmt$^1$]DALDA (1.1 pmol) (FIG. 4), but not DALDA (240 pmol) (FIG. 5).

Behavioral Effects: Rigidity of the caudal part of the body was observed in each animal that received the higher dose (see study 3) of MOR, DALDA, or [Dmt$^1$]DALDA. Four rats in the group that was given the higher dose of DALDA and had a minimum VE less than 60% of baseline (FIG. 3) showed sedative effects that coincided with the period of respiratory depression. During this period, normal activity was markedly suppressed in these animals and they could not negotiate a 60° mesh (Shimoyama et. Al., 1997). However, they retained their righting reflex. No overt sedative effects were observed in animals of other groups.

Figure 6:
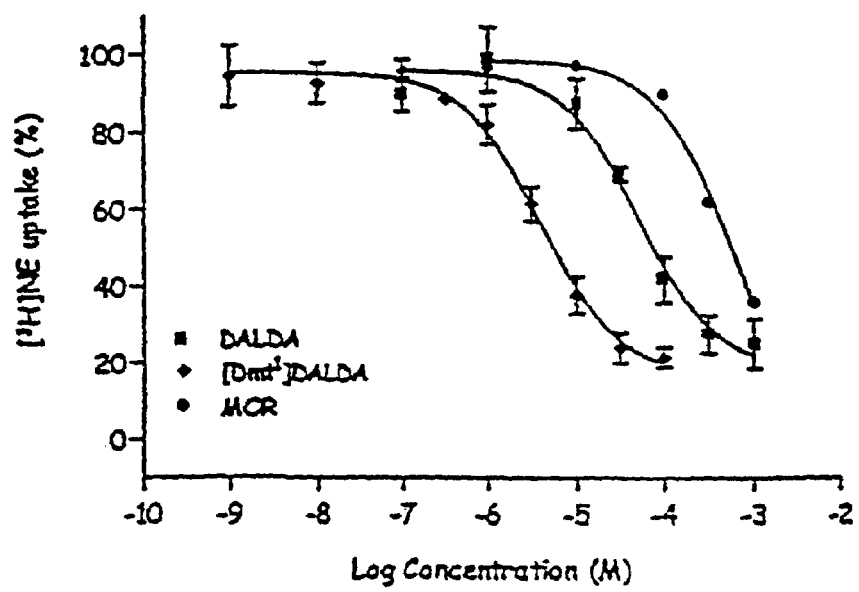
FIG. 6. Effects of MOR, DALDA, and [Dmt[1]]DALDA on NE uptake is spinal cord synaptosomes. Each value represents the mean±S.E. determined from three to five experiments. The $IC_{50}$ values for [Dmt[1]]DALDA, DALDA, and MOR were 4, 54, and 870 μg, respectively.

Inhibition of NE and 5-HT Uptake in Spinal Cord Synaptosomes. DALDA, [Dmt$^1$]DALDA, and MOR all inhibited [$^3$H]NE uptake in a dose-dependent manner (FIG. 6). The $IC_{50}$ for inhibition of [$^3$H]NE uptake was 4.1 μM (2.5-6.7) for [Dmt$^1$]DALDA, 54 μM (28-107) for DALDA, and 870 μM (197-3832) for MOR. At a dose of $10^{-4}$ [Dmt$^1$]DALDA inhibited [$^3$H]NE uptake by 80.6±1.5%. Neither DALDA nor [Dmt$^1$]DALDA had any effect on 5-HT uptake in spinal cord synaptosomes (data not shown).

TABLE 3

The occurrence of respiratory depression after intrathecal administration of MOR, DALDA, and [Dmt$^1$]DALDA

| Drug | Dose | Total No. of Rats | No. of Rats with Low Minimum VE | Time of Occurrence of Low Minimum VE |
|---|---|---|---|---|
| Saline | | 7 | 0 | |
| Morphine | 10 nmol | 6 | 1 | 4 h after administration |
| | 100 nmol | 10 | 4 | 3-5 h after administration |
| DALDA | 0.7 nmol | 6 | 4 | 3-5 h after administration |
| | 7 nmol | 8 | 4 | 3-5 h after administration |
| [Dmt$^1$]DALDA | 3.4 pmol | 6 | 0 | |
| | 34 pmol | 7 | 1 | 3 h after administration |

Example 3

Experimental Methods for Determining Analgesic Potency of Subcutaneous [Dmt¹]DALDA in Mice Antinociceptive Assay.

The antinociceptive assay was a modification of the radiant tail-flick test described by Tulunay and Takemori (1974). The data were made quantal by designating apositive antinociceptive response as one exhibiting an increased latency to tail-flick of at least 3 SD above the mean latency of animals not given the drug.

Intrathecal Injections.

Drugs were injected i.t. (Hylden and Wilcox, 1980) in a volume of 5 ul/mouse, and the latencies measured 30 min after the injections.

Tolerance Measurement.

Mice were made tolerant to morphine by s.c. implantation of one morphine pellet (containing 75 mg morphine free base) for 72 hr. The degree of tolerance was determined as the ratio of the AD50 value of agonist in morphine-pelletted mice to that of placebo-pelletted mice (Way et al., 1969). The implanted morphine pellet was left intact during the antinociceptive assay.

Example 4

Experimental Methods for Determining in Vitro and in Vivo Pharmacokinetics of DALDA and [Dmt¹]DALDA in Sheep Animal Preparation Chronic indwelling catheters were surgically placed in the descending aorta and inferior vena cava of adult female sheep under epidural anesthesia. Five or more days were allowed for recovery from surgery prior to experimental studies.

Compounds [Dmt¹]DALDA was prepared by solid-phase synthesis as described previously (Schiller et al., 2000). For the synthesis of the deuterated peptide analogs, Boc-Phe ($d_5$)—OH was used in place of Boc-Phe-OH. Pentadeuterophenylalanine was purchased from C/D/N Isotope, Vaudreuil, Quebec, Canada and was converted to Boc-Phe($d_5$)—OH by reacting with di-tert-butyldicarbonate. The deuterated peptides were purified by semi-preparative reversed-phase HPLC (Schiller et al., 1989). The purity of all peptides was verified by fast atom bombardment-mass spectrometry (FAB-MS), and the correct amino acid sequence was confirmed by tandem mass spectrometry (Schiller et al., 1989).

In vitro degradation studies To study the degradation of the three peptide analogs in blood, DAMGO (50 µg), DALDA (10 µg) or [Dmt¹]DALDA (10 µg) was added to 25 ml of freshly collected sheep blood, and the mixture was incubated in a water bath at 37° C. Three ml of blood was removed from the blood sample at 15 s and at 5, 15, 30, 60 and 120 min after peptide addition. The blood sample was gently mixed throughout the entire incubation period.

In vivo pharmacokinetic studies In order to avoid the rapid distribution phase associated with intravenous bolus administration, all three peptides were administered as constant rate intravenous infusions to sheep. Based on the known elimination half-life of ~1.5 hr for DALDA (Szeto et al., 1998), it was estimated that a 4-hr infusion would allow plasma drug levels to approach steady state levels. DALDA (0.6 mg/kg/hr) and [Dmt¹]DALDA (0.06 mg/kg/hr) were, therefore, infused via the venous catheter for a period of 4 hr. [Dmt¹]DALDA was infused at a lower dose because it was found to be 200-fold more potent than DALDA after intrathecal administration in the rat tail flick test (Shimoyama et al., submitted for publication) and 100-fold more potent than DALDA in increasing blood pressure in sheep (unpublished data). The current limit of sensitivity of the analytical method prevented the use of an even lower dose of [Dmt¹]DALDA. Blood samples (5 ml) were collected from the arterial catheter at 0, 1, 2, 3, 3.5, 4, 4.25, 4.5, 5, 6 and 7 hr. Because preliminary data showed much more rapid elimination of DAMGO in sheep, DAMGO (0.6 mg/kg/hr) was only infused for 3 h, and blood samples were collected at 0, 0.5, 1, 2, 2.5, 3, 3.25, 3.5, 3.75, 4 and 4.5 hr.

Quantitative analysis of DAMGO, DALDA and [Dmt¹] DALDA All blood samples were collected into chilled borosilicate glass tubes that contained EDTA, and were centrifuged; the plasma was stored in glass containers with teflon-lined caps, and was frozen at −80° C. until processed. All three peptides were purified by HPLC and quantified with mass spectrometry. Details of the quantitative method for DALDA and DAMGO have been published (Grigoriants et al., 1997; Desiderio et al., 2000) and will only be presented briefly here. All plasma samples were deproteinated and eluted through a solid phase extraction cartridge (Sep-Palc C18, Millipore Corp., Milford, Mass.) with $CH_3CN$. An internal standard, the respective deuterated peptide analog (H-Tyr-DAla-Gly-MePhe($d_5$)-Gly-ol, H-Tyr-D-Arg-Phe($d_5$)-Lys-$NH_2$, or H-Dmt-D-Arg-Phe($d_5$)Lys-$NH_2$), was added to each plasma sample before deproteinization. The filtered plasma sample was chromatographed on an RP-analytical column (Delta Pak, 5 µ, C18, 150×3.9 mm, Waters, Milford, Mass.) at a flow rate of 1.5 ml mind$^{-1}$, and UV absorption was monitored at 200 nm (Varian Assoc. Inc., Walnut Creek, Calif.). Gradient elution (7→30% acetonitrile in 0.1% trifluoroacetic acid; 30 min) was used. One-minute fractions were collected, and each fraction was lyophilized for MS analysis. A matrix-assisted laser desorption/ionization (NALDI) time-of-flight (TOF) mass spectrometer (Voyager™-DE RP Biospectrometry Workstation, PerSeptive Biosystems Inc, Framingham, Mass.) was used to quantify the peptide in each plasma sample. The (M+H)+ ion current for each peptide was compared to the ion current from the $d_5$-peptide. $(M+H)^+$ data were used to quantify DALDA and [Dmt¹]DALDA; no intense signal that included the d5 label was available. A 9:1 signal-to-noise (S/N) ratio was found for DALDA and [Dmt¹] DALDA at a concentration of 375 fmol/µl. Recalculating to a 3:1 S/N ratio, a limit of detection of 125 fmol/µl is available. A post-source decay (PID) fragment was available for DAMGO. An S/N ratio of 10:1 was measured at 4 pmol/µl. Thus, a calculated limit of detection of 400 fmol/µl is available Pharmacokinetic Analyses Plasma levels of DAMGO, DALDA and [Dmt¹]DALDA during and after the 4 h infusion were subjected to compartmental analysis using nonlinear regression (WINNONLIN). The derived pharmacokinetic constants were used to calculate the apparent volume of distribution at steady state (Vd), elimination half-life ($t_{1/2}$) and clearance (CL). Example 5

Experimental Methods for Determining Whether DALDA and [Dmt¹]DALDA are Substrates for the Peptide Transporter PEPT2.

Rat PEPT2 is expressed in HeLa cells heterologously by using the vaccinia virus expression technique. HeLa cells do not express any peptide transport system endogenously. The activity of the heterologously expressed PEPT2 in these cells is measured by monitoring the uptake of the model dipeptide glycylsarcosine (50 micromolar) in the presence of an inwardly directed proton gradient. The proton gradient is the driving force for the peptide transporter. Therefore, the uptake buffer used in these studies is 25 mnM Mes/Tris (pH 6.0) containing 140 mM NaCl, 5.4 mM KC1, 0.8 mM MgSO4, 1.8 mM CaC12 and 5 mM glucose. HeLa cells that were transfected with empty vector (pSPORT) serve as controls. The uptake of glycylsarcosine in these control cells is subtracted from the uptake in ratPEPT2 cDNA-transfected cells to calculate the uptake that is mediated specifically by rat PEPT2. We performed a dose-response experiment for DALDA and superDALDA over a concentration range of 10-1000 micromolar. The data from these dose-response experiments were used to calculate the IC50 values for these two compounds.

Example 6

Description of Studies Showing [Dmt¹]DALDA does not Increase Blood Pressure if Administered as a Constant Rate Intravenous Infusion.

Earlier studies showed that [Dmt¹]DALDA produces a transient increase in blood pressure in awake sheep when administered as an intravenous bolus at doses ranging from 0.003-0.009 mg/kg. Even a brief period of increased blood pressure may be a risk factor in patients with hypertension, compromised myocardial function (such as after a myocardial infarction) or patients who are at risk for strokes. The response is short-lasting because the receptor desensitizes rapidly. We can take advantage of this rapid desensitization and eliminate the blood pressure response by administering the drug as a slow intravenous infusion rather than as a rapid bolus injection.

Studies have been carried out in sheep whereby [Dmt¹] DALDA was infused intravenously at a constant rate ranging from 0.06-0.6 mg/kg/h for as long as 4 h. There was no significant change in blood pressure observed at any time during or after the drug infusion. Thus the increase in blood pressure can be avoided by using a slow intravenous infusion of [Dmt¹]DALDA.

Example 7

Experimental methods for determining effects of DALDA and [Dmtl]DALDA in Inhibiting Norepinephrine Uptake in Cardiac and Spinal Cord Synaptosomes Preparation of Heart and Spinal Cord Synaptosome Adult female Hartley strain guinea pigs (440-550 g) were decapitated and the spinal cords taken out. A crude synaptosomal (P2) fraction was prepared as described previously (Lonart and Johnson 1995; Li 2000). Briefly, the tissue was minced and homogenized in 10 ml of ice-cold 0.32 M sucrose solution (pH 7.4) with a Thomas B075 homogenizor, clearance 0.13-0.18 mm. The homogenate was centrifuged for 10 min at 1,200×g in a Megafuge centrifuge at 4° C. The resulting supernatant was then centrifuged at 20,000 ×g for 20 min in JA-17 rotor of a Beckman J2-21 centrifuge at 4° C. and the supernatant discarded. The pellet (P2) was gently resuspended in aerated (100% $O_2$) ice-cold buffer contairing (in mM):HEPES 20, NaCl 140, KCl 5, $NaHCO_3$ 5, $MgCl_2$ 1, $Na_2HPO_4$ 1.2, $CaCl_2$ 1.2 and glucose 10, pH 7.4, and centrifuge at 3,000×g for 12 min in a Megafuge at 4° C. Pour out the supernatant. Gently resuspend synaptosome in 10 ml buffer with the aid of a Dotince homogenizor just before using. Protein concentration was determined by the method of Bradford (1976) at 595 nm using bovine serum albumin as a standard in a Spectra Max plus machine (Molecular Device Co. Sunnyvale, Calif.)

Uptake Experiments

Add buffer 0.6 ml in tubes, synaptosome solution 0.2 ml (about 100 μg), then varying concentration of drug 0.1 ml (each concentration performed in triplicate), put in water bath for pre-incubation for 10 min at 37° C. The uptake was initiated by the addition of [$^3$H]NE (100 nM) or [$^3$H]5-HT (50 nM) 0.1 ml, continued to incubate for 6 min and terminated by a rapid cooling of sample tubes in ice-cold water for 3 min. The synaptosome were then collected using a Harvest machine with GF/B filter, washed for 3 times with ice-cold 150 mM Tris HCl buffer (pH 7.4) 2 ml. After drying, put filter in scintillation liquid vials then add scintillation liquid 6 ml. Filter-bound radioactivity was counted by liquid scintillation counter (Becklman LS6001). The difference in [$^3$H]NE or [$^3$H]5-HT accumulation at 37° C. and 0° C. was taken as a measure of active uptake.

Data Analysis

Results represent with mean values±SEM of at least three to five independent experiments. The $IC_{50}$ were calculated by GraphPad Prism program and also represent with 95% confidence intervals.

Drugs

1-[7,8-$^3$H]Norepinephrine (specific activity 1.37TBq/ mmol, radiochemical purity 93.2%), and 5-hydroxy[$^3$H] trytamine trifluoroacetate (specific activity 4.00TBq/mmol, radiochemical purity 99%) were purchased from Amersham Phannacia Biotech Co. (Buckingharnshire, England). Desipramine hydrochloride, fluoxetine hydrochloride and morphine sulfate were bought from Sigmra Co. (St. Louis, Mo.). DynorphinA(1-13), DAMGO were obtained from NIH. [Dmt¹]DALDA and DALDA are synthesized by methods known in the art. See, for example, Brown, et al, U.S. Pat. No. 5,602,100 and the example below.

Example 8

Peptide Synthesis

Peptides are synthesized by the solid-phase method using tert-butyloxycarbonyl (Boc)-protected amino acids and 1,3-diisopropylcarbodiimide (DIC)/1-hydroxybenzotriazole (HOBt) as coupling agents. Boc-Tmt is prepared by methods kcnown in the art. 2'-methylphenylalanine can be prepared from 1,2,3,4-tetrahydroisoquinoline-3-carboxylic acid (Tic) with minimal racemization (8%) by carrying out the hydrogenolysis at 60° C. using 10% Pd/C and 4 atm $H_2$ pressure. Under the latter conditions, 2'-methyltyrosine (Mmt) is prepared from Tic(OH) in good yield (48%) and with minimal racemization (<10%). Racemic 2'-hydroxy-6'-methyltyrosine is synthesized by methods known in the art. The bis-Boc derivative of Mmt and the tris-Boc derivative of D,L-Hmt are prepared by reaction with di-tert-butyl dicarbonate in the presence of triethylamine (TEA) and 4-dimethylaminopyridine (DMAP). The tris-Boc derivative of D,L-Hmt is incorporated into the peptide in racemic form. Peptides are cleaved from the resin by HF/anisole treatment in the usual manner. Peptide purification and separation of the diasteromeric peptides in the case of the Hmt[1]-analogue were achieved by preparative reversed phase HPLC.

What we claim is:

1. A method for protecting a mammal's heart from ischemic-reperfusion injury in a mammal in need thereof, the method comprising administering to the mammal an effective amount of 2',6'-dimethyl-Tyr-D-Arg-Phe-Lys-$NH_2$ peptide; wherein said effective amount is effective to protect the mammal's heart from ischemic reperfusion injury.

2. The method according to claim 1, wherein the mammal is a human.

3. The method according to claim 1, wherein the peptide is administered via constant rate intravenous infusion.

4. The method according to claim 1, wherein said peptide is mixed with a suitable pharmaceutical carrier.

* * * * *

UNITED STATES PATENT AND TRADEMARK OFFICE
CERTIFICATE OF CORRECTION

PATENT NO. : 7,498,297 B2  Page 1 of 1
APPLICATION NO. : 10/333485
DATED : March 3, 2009
INVENTOR(S) : Szeto et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (776) days Delete the phrase "by 776 days" and insert -- by 995 days --

Signed and Sealed this

Eighth Day of September, 2009

David J. Kappos
*Director of the United States Patent and Trademark Office*